(12) United States Patent
Katti et al.

(10) Patent No.: US 11,426,357 B2
(45) Date of Patent: Aug. 30, 2022

(54) MANGIFERIN ENCAPSULATED GOLD NANOPARTICLES, FABRICATION METHODS AND CANCER THERAPEUTIC METHODS

(71) Applicant: The Curators of the University of Missouri, Columbia, MO (US)

(72) Inventors: Kattesh Katti, Columbia, MO (US); Cathy Cutler, Columbia, MO (US); Menka Khoobchandani, Columbia, MO (US); Kavita Katti, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 16/339,304

(22) PCT Filed: Oct. 3, 2017

(86) PCT No.: PCT/US2017/054945
§ 371 (c)(1),
(2) Date: Apr. 3, 2019

(87) PCT Pub. No.: WO2018/067570
PCT Pub. Date: Apr. 12, 2018

(65) Prior Publication Data
US 2019/0290594 A1     Sep. 26, 2019

Related U.S. Application Data

(60) Provisional application No. 62/403,780, filed on Oct. 4, 2016.

(51) Int. Cl.
| | | |
|---|---|---|
| A61K 9/51 | (2006.01) |
| A61P 35/00 | (2006.01) |
| A61K 9/00 | (2006.01) |
| A61K 51/04 | (2006.01) |
| A61K 51/12 | (2006.01) |
| B22F 9/24 | (2006.01) |
| B22F 1/054 | (2022.01) |
| B22F 1/102 | (2022.01) |
| B22F 1/0545 | (2022.01) |
| B82Y 5/00 | (2011.01) |

(52) U.S. Cl.
CPC .......... *A61K 9/5192* (2013.01); *A61K 9/0019* (2013.01); *A61K 9/5115* (2013.01); *A61K 51/0491* (2013.01); *A61K 51/1244* (2013.01); *A61P 35/00* (2018.01); *B22F 1/054* (2022.01); *B22F 1/0545* (2022.01); *B22F 1/102* (2022.01); *B22F 9/24* (2013.01); *A61K 2121/00* (2013.01); *B82Y 5/00* (2013.01)

(58) Field of Classification Search
CPC ...... A61K 9/51; A61K 9/5107; A61K 9/5138; A61K 9/5161; A61K 9/5115; A61K 9/5192; A61K 9/5005; A61K 9/501
See application file for complete search history.

(56) References Cited

U.S. PATENT DOCUMENTS

| | | |
|---|---|---|
| 8,211,205 B1 | 7/2012 | Didenko et al. |
| 8,569,063 B1 | 10/2013 | Sahi et al. |
| 2007/0051202 A1 | 3/2007 | Raghuraman et al. |
| 2009/0074674 A1 | 3/2009 | Katti et al. |

FOREIGN PATENT DOCUMENTS

| | | |
|---|---|---|
| CA | 2660507 | 12/2017 |
| CN | 104070179 | 10/2014 |
| WO | 2013141722 | 9/2013 |
| WO | 2016046845 | 3/2016 |

OTHER PUBLICATIONS

Of Al-Yasiri (Synthesis and evaluation of radioactive gold nanoparticles for cancer treatment and imaging; PhD Dissertation to University of Missouri—Columbia, May 2015, hereafter Al-Yasiri) (Year: 2015).*
Philip (Rapid green synthesis of spherical gold nanoparticle using mangifera indica leaf; Spectochimica Acta Part A 77, 2010, 807-810) (Year: 2010).*
Katti et al (Hybrid Gold Nanoparticle in Molecular Imaging and Radiotherapy; Czechoslovak Journal of Physics, vol. 56 2006) (Year: 2006).*
Herizchi et al (Current methods for synthesis of gold nanoparticles, Artificial Cells, Nanomedicine, and biotechnology, 2016, 44:596-602) (Year: 2016).*
Kannan et al (Functionalized radioactive gold nanoparticles in tumor therapy, Wiley Interdiscip Rev Nanomed Nanobiotechnology, Jan.-Feb. 2012; 4, 42-21). (Year: 2012).*
Cutler et al (Comparison of in vivo uptake of radioactive gold nanoparticles formulated using phytochemicals; The Journal of Nuclear Medicine, May 2015, 56, 1267) (Year: 2015).*
Shah et al., "Mangifera Indica (Mango)", Pharmacognosy Review, 2010, pp. 1-14, vol. 4, No. 7, Pharmacognosy Reviews.
Philip, "Rapid green synthesis of spherical gold nanoparticles using Mangifera indica leaf", Spectrochimica Acta Part A: Molecular and Biomolecular Spectroscopy, 2010, pp. 807-810, vol. 77, Elsevier B.V.

(Continued)

*Primary Examiner* — Micah Paul Young
(74) *Attorney, Agent, or Firm* — Greer, Burns & Crain, Ltd.; Steven P. Fallon

(57) ABSTRACT

A method for forming encapsulated gold nanoparticles mixes mangiferin into a liquid medium to form a reducing agent solution. Gold salts are mixed into the reducing agent solution. Reaction of the gold salts is permitted, in the absence of any other reducing agent, to form a nanoparticle solution of stabilized, biocompatible gold nanoparticles coated with mangiferin. The gold salts can consist of AuCl4, or can consist of radioactive gold salts. A cancer therapy method injects a solution of mangiferin encapsulated gold nanoparticles directly into a solid tumor. A solution consisting of an aqueous or alcoholic medium and mangiferin encapsulated gold nanoparticles is provided. The mangiferin encapsulated gold nanoparticles can have core sizes of ~5-20 nm and total sizes of ~20-120 nm.

16 Claims, 5 Drawing Sheets

(56) References Cited

OTHER PUBLICATIONS

Joshi et al., "Early Human Safety Study of Turmeric Oil (*Curcuma longa* Oil) Administered Orally in Healthy Volunteers", Journal of the Association of Physicians of India, Nov. 2003, pp. 1055-1060, vol. 51.

Nair et al., "Delivery of anti-inflammatory nutraceuticals by nanoparticles for the prevention and treatment of cancer", Biochemical Pharmacology, Dec. 15, 2010, pp. 1-26, vol. 80, No. 12, Elsevier Inc.

International Search Report and Written Opinion from the corresponding International Patent Application No. PCT/US2017/054945, dated Nov. 12, 2017.

International Search Report and Written Opinion from the corresponding International Patent Application No. PCT/US2018/017421, dated Apr. 2, 2018.

Indian Office Action from the corresponding Indian Patent Application No. 201947017150, dated Feb. 26, 2020.

Gold-Smith et al., "Magniferin and Cancer: Mechanisms of Action", Nutrients, 2016, pp. 1-25, vol. 8, No. 396, MDPI.

Muhammad et al. "Green Synthesis of Gold Nanoparticles and Their Characterizations Using Plant Extract of Papaver somniferum", Nano Science & Nano Technology: An Indian Journal, Sep. 7, 2017, pp. 1-8, vol. 11, No. 2., Trade Science Inc.

\* cited by examiner

MANGIFERIN ENCAPSULATED GOLD NANOPARTICLES, FABRICATION METHODS AND CANCER THERAPEUTIC METHODS

PRIORITY CLAIM AND REFERENCE TO RELATED APPLICATION

The application claims priority under 35 U.S.C. § 119 and all applicable statutes and treaties from prior provisional application Ser. No. 62/403,780, which was filed on Oct. 4, 2016.

FIELD

Fields of the invention include gold nanoparticles, nanomedicine and cancer therapy. An example application of the invention is immunotherapy for the treatment of prostate cancer and other solid tumors that have elevated NF-κB signaling.

BACKGROUND

Patients with localized prostate cancer are often successfully treated via surgery or radiotherapy while those with metastatic conditions are treated through androgen deprivation therapy (ADT). See, A. J. Chang, K. A. Autio, M. Roach, 3rd and H. I. Scher, "High-risk prostate cancer-classification and therapy," Nat Rev Clin Oncol. 11:308-23 (2014). There is an emerging consensus that current therapies are poorly effective for patients with castration-resistant prostate cancer (CRPC), where the disease manifests from asymptomatic or minimally symptomatic, non-metastatic disease to symptomatic or highly metastatic condition, depending on the time of diagnosis with significant inter-patient variation. The United States Food and Drug Administration (FDA) has approved several chemotherapeutic agents including docetaxel, cabazitaxel, abiraterone, and enzalutamide for treating such patients. Drug resistance attributable to modulation of myeloid-derived suppressor cells (MDSCs) is seen in a significant proportion of patients. See, Y. Rong, C. H. Yuan, Z. Qu, H. Zhou, Q. Guan, N. Yang, et al., "Doxorubicin resistant cancer cells activate myeloid-derived suppressor cells by releasing PGE2," Sci Rep. 6:23824 (2016). MDSCs induce an immune suppressive microenvironment and promote the M2-polarized tumor associated macrophages (TAMs) that support angiogenesis and metastasis. Numerous studies have shown that tissue and serum exosomes from prostate cancer patients induced higher levels of macrophage polarization into an alternatively activated M2 phenotype. See, P. C. Chen, H. C. Cheng, J. Wang, S. W. Wang, H. C. Tai, C. W. Lin, et al., "Prostate cancer-derived CCN3 induces M2 macrophage infiltration and contributes to angiogenesis in prostate cancer microenvironment" Oncotarget, 5:1595-608 (2014). Therefore, cancer treatment emphasizing personalized therapy through precision medicine, and immune checkpoint blockade that targets M2 macrophage is distinguished from a plethora of "common denominator" treatment approaches in current use. There is an important and urgent unmet clinical need that combines different immunotherapeutic approaches, to reap synergistic therapeutic benefits for cancer patient populations. In the context of developing novel therapies for treating drug resistant CRPC, effective targeting of (TAMs) assumes a central focus, because experimental results indicate that TAMs are major contributors to drug- and radio-protective effects, and that an elevated number of TAMs and their M2 profile are correlated with therapy failure and poor prognosis in prostate cancer patients. See, B. Ruffell and L. M. Coussens, "Macrophages and therapeutic resistance in cancer," Cancer Cell. 27:462-72 (2015).

Prostate and most solid tumors have elevated NF-κB signaling, upregulated by the release of cytokines by M2 macrophages in the tumor microenvironment. Compelling evidence shows that chemotherapeutic treatment of solid cancers in general, and prostate tumors in particular, activates NF-κB, a key transcription factor which plays a critical role in the development and progression of cancer and consequently aiding chemo and multi therapy drug resistance. Upregulated NF-κB activity can upregulate pro-survival pathways, including BCL-2. Mangiferin (MGF) has been shown in independent studies to inhibit both NF-κB and BCL-2. Mangiferin was administered orally. See, F. Gold-Smith, A. Fernandez and K. Bishop, "Mangiferin and Cancer: Mechanisms of Action," Nutrients. 8 (2016). The authors noted that other anti-cancer agents had been encapsulated to improve pharmacokinetic properties. The authors also discussed, on page 19, the need for a "smart vehicle" for mangiferin delivery to tumor cells, while noting that such a vehicle did not exist and that such a vehicle would have to be unique to mangiferin.

Recent studies have shown the relationship of NF-κB to the survival of cancer cells and the response of immune cells to cancer. B. Kuhnemuth, L. Muhlberg, M. Schipper, H. Griesmann, A. Neesse, N. Milosevic, et al., "CUX1 modulates polarization of tumor-associated macrophages by antagonizing NF-κB signaling," Oncogene. 34:177-87 (2015). Cancer stem cells also manifest activated NF-κB, thus contributing to the promotion of a pro-inflammatory environment leading to inhibition of apoptosis. Activated NF-κB polarizes macrophages towards the alternatively activated M2 phenotype responsible for catalyzing tumor growth and even bringing about resistance to drug treatment. The present inventors have recognized that the direct correlation of NF-κB in triggering M2 macrophages in prostate tumor angiogenesis, invasion, metastasis, immunosuppression, and chemotherapeutic treatment resistance singularly and collectively makes a compelling case for the design of NF-κB- and TAM-M2-macrophage-targeting drug.

Increasing evidence from clinical data has lead the present inventors to hypothesize that macrophages in human prostate cancer patients contribute both to the primary tumor growth and to the subsequent development of metastasis. In patients with Gleason Score (GS) 7 to 8-10 and pT3a stages, higher density of macrophages found in primary prostate tumor sites were characterized to be of the M2 macrophage phenotype. M2 macrophages within the tumor microenvironment (TAM) promote angiogenesis, tumor growth, and metastasis ultimately leading to the transition into castration-resistant prostate cancer (CRPCa) and poor prognostic disease state. Several investigations have concluded that to achieve effective immunomodulatory effects by immunotherapeutic agents it is important to develop intratumoral delivery technologies of immunotherapeutic agents to reach the immune-suppressive effector cells, including M2 macrophages, which are localized within the tumor microenvironment. Indeed, there is preclinical and clinical evidence suggesting that therapeutic systemic antitumor immune response is better when immunotherapeutic agents are delivered through intratumoral immunomodulation rather than systemically. See, K. Van der Jeught, L. Bialkowski, L. Daszkiewicz, K. Broos, C. Goyvaerts, D. Renmans, et al., "Targeting the tumor microenvironment to enhance antitumor immune responses" Oncotarget 6:1359-81 (2015). Classical methods such as catheterization for continuous delivery or slow-release of PEGylated drugs intratumorally are regaining favor as an approach. Nanomolecule immunotherapeutic platforms which allow efficient penetration across the tumor vasculature due to their size, active (receptor mediated) and passive (enhanced permeation and retention (EPR)) targeting to achieve uptake and retention of optimal doses are being developed.

The present inventors and colleagues have previously developed stabilized gold nanoparticles encapsulated with proteins, peptides and small molecules. See, M. Khoobchandani, K. Katti, A. Maxwell, W. P. Fay and K. V. Katti, "Laminin Receptor-Avid Nanotherapeutic EGCg-AuNPs as a Potential Alternative Therapeutic Approach to Prevent Restenosis," Int J Mol Sci. 17, (2016); R. Shukla, N. Chanda, A. Zambre, A. Upendran, K. Katti, R. R. Kulkarni, et al., "Laminin receptor specific therapeutic gold nanoparticles (198AuNP-EGCg) show efficacy in treating prostate cancer," Proc Natl Acad Sci USA. 109:12426-3 (2012). Such nanoparticles were demonstrated to be retained in tumors through measurement of the gamma emission of Au-198 encapsulated nanoparticles, which allowed precise estimation of gold within tumor cells/tumor tissues down to sub nanomolar concentrations through scintigraphic counting techniques.

The present inventors have previously demonstrated stabilized gold nanoparticles that were encapsulated with polyphenol-flavonoids. Katti et al US Patent Publication US 2012/0134918 discloses Gum Arabic (GA) coated $^{198}$Au nanoparticles, a method of making and a therapeutic and imaging agent. Katti et al. U.S. Pat. No. 8,333,994 discloses formation of gold nanoparticles via reduction using black tea, turmeric, curcumin or cinnamon or a similar naturally occurring polyphenols- or flavanoids-rich plant material. Katti U.S. Pat. No. 9,358,310 discloses stabilized, biocompatible gold nanoparticles that are stabilized with material from epigallocatechin Gallate (EGCg). These patents demonstrated that polyphenols- or flavonoids-rich plant material can be used to reduce gold salts and produce stabilized gold nanoparticles.

Mangiferin (1,3,6,7-tetrahydroxyxanthone-C2-D glucoside) is a xanthonoid that is attached to a sugar. It is a polyphenol functionalized-D-glucoside-xanthone family of phytochemical found in abundance in the Anacardiaceae and Gentianaceae family of plant species, especially in mangoes skin and honeybush tea. See, F. Gold-Smith, A. Fernandez and K. Bishop, "Mangiferin and Cancer: Mechanisms of Action," Nutrients. 8 (2016). Mango leaves have been ingested as a natural medicine for centuries in various cultures. Recent in vitro and in vivo broad spectrum anti-tumor investigations of mangiferin have been correlated with its versatile anti-inflammatory, immunomodulatory, cell cycle arrest, anti-proliferative, anti-apoptotic, anti-oxidative, anti-genotoxic, and anti-viral characteristics. Gold-Smith et al., supra. A study has attributed mangiferin to reduced tumor volumes in comparable magnitude, and as a possible D-glucoside-xanthone structural motif for cancer therapy. Gold-Smith et al., supra. Anti-angiogenesis, pro-apoptotic and cumulative antitumor properties have been theorized to result from the immunomodulatroy ability of this phytochemical to inhibit NFκB, target TAM and downstream signaling pathways responsible for tumor progression and metastases. Gold-Smith et al., supra. Ingestion of mangiferin has shown mild to non-existent side effects. While a possible cancer therapeutic utility has been recognized for mangiferin, rapid metabolic degradation of this phytochemical in vivo has remained as a significant barrier to achieving clinically relevant levels for effective cancer therapy.

SUMMARY OF THE INVENTION

An embodiment of the invention is a method for forming encapsulated gold nanoparticles that mixes mangiferin into a liquid medium to form a reducing agent solution. Gold salts are mixed into the reducing agent solution. Reaction of the gold salts is permitted, in the absence of any other reducing agent, to form a nanoparticle solution of stabilized, biocompatible gold nanoparticles coated with mangiferin. The gold salts can consist of AuCl4, or can consist of radioactive gold salts. Preferably, the concentration of mangiferin in the reducing agent solution is in the range of 1.6-3.3 mM (millimoles), and the concentration of gold salt is 1.7-3.4 mM. Preferably, the permitting reaction is conducted at an agent solution temperature of 80° C.-100° C.

The invention provides a cancer therapy method that injects a solution of mangiferin encapsulated gold nanoparticles directly into a solid tumor. The invention also provides a solution consisting of an aqueous or alcoholic medium and mangiferin encapsulated gold nanoparticles is provided. The mangiferin encapsulated gold nanoparticles can have core sizes of ~5-20 nm and total sizes of ~20-120 nm.

Preferred methods of the invention include direct injection into solid tumors, however, the MGF-$^{198}$AuNP have therapeutic efficacy for treating various solid, liquid, localized and metastatic tumors comprising of breast, cervical, glioblastomas, liver, melanoma, osteosarcomas, pancreatic, prostate and all related tumors and neoplastic diseases in humans and animals. Additional methods of treatment include introducing MGF-$^{198}$AuNPs into an animal or human for treatment of such various solid, liquid, localized and metastatic tumors.

DETAILED DESCRIPTION OF THE PREFERRED EMBODIMENTS

Figure 1:
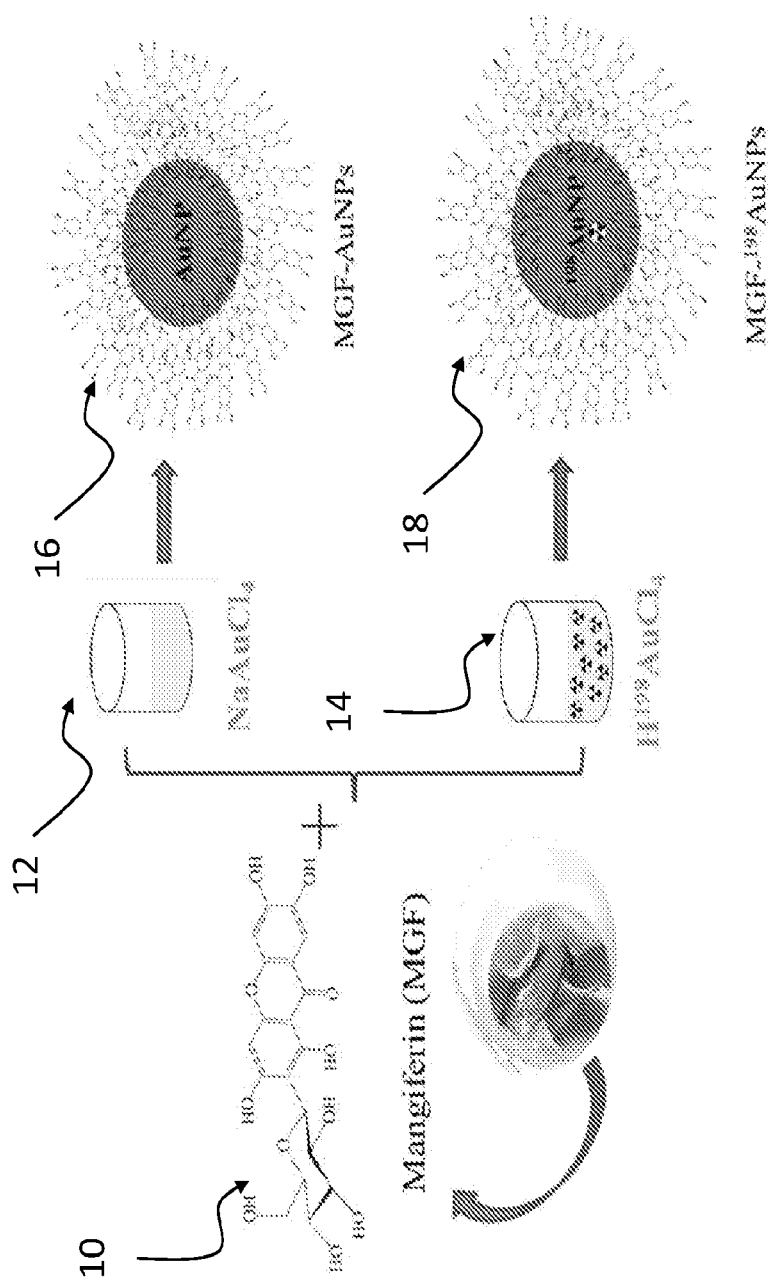
FIG. 1 is a schematic illustration of a preferred synthesis process for both MGF-AuNP (mangiferin non-radioactive Au nanoparticles) and MGF-$^{198}$AuNP (mangiferin radioactive Au nanoparticles) in accordance with the invention.

An embodiment of the invention is a method for forming gold nanoparticles encapsulated in mangiferin, including non-radioactive gold nanoparticles and $^{198}$Au nanoparticles. The preferred method leverages redox properties of the antioxidant mangiferin to reduce gold salt to produce the encapsulated gold nanoparticles. The preferred interaction of gold salt with mangiferin in water results in well-defined mangiferin encapsulated gold nanoparticles. Experiments have demonstrated the present mangiferin encapsulated gold nanoparticles are stable under in vitro profiles. Experiments have also demonstrated that the present mangiferin encapsulated gold nanoparticles have affinity and selectivity toward Laminin receptors which are over expressed in prostate (and colorectal, pancreatic, breast cancers) and a host of other laminin receptor positive mammalian and human cancers. The invention also provides stabilized mangiferin encapsulated gold nanoparticles, and a kit including a solution of the mangiferin encapsulated gold nanoparticles for direct intratumoral injection.

The present invention provides a surprising result in view of prior work of the present inventors and colleagues using polyphenols such as epigallocatechin Gallate (EGCg) and flavonoids-rich plant materials, which have the propensity to reduce gold salt to produce the corresponding gold nanoparticles. Mangiferin, which has xanthanoid and glucose chemical functionalities, is expected to behave differently. The glucose end of mangiferin is expected to reduce gold salt and the xanthanoid can also reduce the gold salt. The combined reducing power of both xanthanoid and the glucose units is strong and such chemical reactions are expected to result in the complete conversion of gold salt into the corresponding gold metal. Contrary to this expectation, the present invention demonstrated in experiments that the xanthanoid and the glucose units in magiferin work in synergy to transform gold salt into the corresponding gold nanoparticles with subsequent stabilization of gold nanoparticles. The mangiferin in a solution acts as a reducing agent in the absence of any other reducing agent. No harsh chemicals are required.

The invention leverages beta rays from radioactive gold nanoparticles, functionalized and stabilized with mangiferin, for treating cancer. The present inventors have determined that the beta energy of radioactive gold nanoparticles is responsible for cancer treatment, demonstrated in experiments. The present inventors have also demonstrated through experiments that, while inhibition of NF-κB and BCL-2 via mangiferin can provide some anti-tumor effects, the overall cancer therapy, is solely due to the beta energy of radioactive gold nanoparticles which have an affinity for tumor cells.

A preferred therapeutic method of the invention is direct intratumoral injection of stabilized mangiferin encapsulated gold nanoparticles into a solid tumor, such as a prostate tumor. Experiments have demonstrated that direct administration of mangiferin-conjugated gold nanoparticles (MGF-AuNPs) intratumorally into prostate tumor in mice controls the growth of prostate tumors effectively. Therefore, this invention provides a new modality for prostate cancer treatment through an innovative nanotechnological-phytomedicine intratumoral direct injection.

The present inventors have discovered and confirmed experimentally that the MGF-AuNPs are smart nanoparticles for use in precision and personalized medicine because they target macrophages and also suppress the NF-κB transcription factor. MGF-AuNPs are nontoxic to normal cells as elucidated through cell viability of Human Aortic endothelial cells (HAECs) after 24 hr incubation with increasing concentrations of these gold nanoparticles. The inventors have also discovered and confirmed experimentally that MGF-AuNPs are selectively toxic to prostate cancer cells (PC-3 of human prostate cancer origin) as shown through incubation with increasing concentrations of nanoparticles.

The mechanism of retention of prior gold nanoparticles discussed in the background functionalized with GA is surprising. Based upon experiments, we believe that the retention can be primarily attributed to the size and charge of the nanoparticles, thus aiding enhanced permeation and retention effects for GA-AuNPs. However, GA-AuNPs, once homed into the tumor cells, begin to leak over a period of 24 hours. This leakage is due to the fact that GA-AuNPs have limited affinity to tumor cell receptors. Compared to GA-AuNPs, EGCG-AuNPs, show significantly higher retention within tumor cells, which can be attributed to the size and charge of these nanoparticles. The EGCG-AuNPs have shown well-defined selective and high affinity to laminin receptors that over expressed on various tumor cells including prostate tumors. This receptor affinity of EGCG-AuNPs provides excellent retention within tumor cells with 10-12% leakage over a 24-hour time period. The present MGF-AuNPs and MGF-$^{198}$AuNPs have been demonstrated in experiments regarding the invention to provide much high retention than even the EGCG-AuNPs, for example showing prostate tumor specificity with over 90% of the injected dose retained in the tumor for over 24 hours.

The present inventors have recognized that, when designing new treatment modalities for prostate cancer, the crosstalk between NF-κB transcription factor and the macrophages in the tumor microenvironment is of paramount importance, and have discovered that the MGF-AuNPs are an effective modality, especially with intratumoral direct injection. Experiments provide evidence of efficacy.

Preferred embodiment MGF-AuNPs include high affinity ligand-conjugated MGF-AuNPs that can provide optimum retention and uptake of therapeutic payloads of immunotherapeutic agents by cancer cells/tumor tissue through receptor-mediated active targeting as well as EPR pathways. We have demonstrated in experiments that the xanthanoid and glucose units of mangiferin—when encapsulated around gold nanoparticles—provide optimum retention of radioactive gold nanoparticles within tumor tissue/cells. This selective and high retention of mangiferin-functionalized gold nanoparticles within tumor cells is explained as uptake of therapeutic payloads of immunotherapeutic agents by cancer cells/tumor tissue through receptor-mediated active targeting as well as EPR pathways.

Example conjugated MGF-AuNPs include immuno-modulating αvβ3-integrin and laminin-receptor-targeting MGF-AuNPs. Although free mangiferin has been recognized for its cytotoxicity and immunomodulatory properties, the present MGF-AuNPs provide a clinically significant pathway to amplify: (i) tumor cell-specific cytotoxicity; (ii) immunomodulatory suppression of NF-κB activation, and (iii) targeting tumor associated alternatively activated M2 macrophages—as elucidated in both in vitro and in vivo prostate tumor models during experiments.

Preferred embodiments of the invention will now be discussed with respect to the experiments. Artisans will recognize broader aspects of the invention from the experiments.

FIG. 1 shows the preferred synthesis process for both MGF-AuNP and MGF-$^{198}$AuNP. Mangiferin 10 is reacted with a solution of gold salts 12 or a solution of radioactive gold salts 14. With conditions and concentrations described below, the mangiferin 10 reduces the gold salts 12 or 14 and produces either MGF-AuNP 16 (AuNP encapsulated with mangiferin) or MGF-$^{198}$AuNP 18 ($^{198}$AuNP encapsulated with mangiferin), with both being represented in FIG. 1.

Without being bound to the theory or the theory being necessary to practice the present invention, the inventors believe that mangiferin functionalized gold nanoparticles home into tumor cells/tumor tissue through at least three different mechanisms. A first mechanism is attributed to the size and charge of these nanoparticles, which thus aids enhanced permeation and retention effects. A second mechanism is attributed to the high metabolism of sugars into tumor cells. Mangiferin includes a sugar structure. A third mechanism is attributed to the fact that the xanthanoid unit in mangiferin provides additional armamentarium for enhanced affinity of MGF-AuNPs toward tumor cells. The inventors believe that these three mechanisms work in tandem to provide unprecedented affinity and retention of MGF-AuNPs into tumor cells, which has been demonstrated through experiments.

Example experimental MGF-AuNPs and MGF-[198]AuNPs were tested for retention. In vivo prostate tumor retention studies demonstrated that mangiferin encapsulation transforms these nanoparticles to be prostate tumor specific with over 90% of the injected dose retained in the tumor for over 24 hours. The retention is surprisingly much higher than prior AuNPs, including GA-AuNPs and EGCG-AuNPs. The inventors have determined that the present MGF-AuNPs, because of their size and charge, accumulate by EPR (enhanced permeability and retention) while the laminin receptor specificity leads to efficient endocytosis within prostate tumor cells, thus augmenting tumor uptake and retention. The data showed prostate tumor avidity of MGF-[198]AuNPs at different time points was significantly higher than GA-AuNPs and EGCG-AuNPs Animal were injected intratumorally in dose of 60 µg/cc volume of prostate tumor to obtain the data.

Experiments showed MGF-AuNP synthesis through a redox pathway that leverages the high antioxidant capacity of Mangiferin to inject electrons into the gold precursor to produce mangiferin encapsulated gold nanoparticles in 100% reproducible reactions. Mangiferin and gold salt ($NaAuCl_4$) are interacted in a liquid medium consisting of water and react to produce MGF-AuNPs. The solution consists of mangiferin, gold salts and the liquid medium of distilled water. Alternative liquid media include alcoholic media and combinations of alcoholic and aqeous media. The process does not require any external reducing agent or stabilizing agent, and consists of the interaction of Mangiferin with gold salt in the liquid medium of water. Mangiferin serves multiple roles of a chemical reductant, encapsulant to stabilize AuNPs, and also provides the immunotherapeutic characteristics of MGF-AuNPs.

UV-visible spectrophotometric analysis confirmed the surface plasmon resonance (SPR) of MGF-AuNPs at 535±2 nm. The core size of MGF-AuNPs was obtained by TEM, and indicated that MGF-AuNPs are spherical, have a typical core size of 35±2 nm, and common narrow dispersions include core sizes in the range of ~20-50 nm, and more generally ~5-50 nm. The results obtained by dynamic light scattering instrument revealed that typical MGF-AuNPs showed hydrodynamic size at 55±5 nm and the zeta potential−40±2 mV. The excess mangiferin from the reaction mixture creates a robust encapsulation around gold nanoparticles thus requiring no external chemical agent for the stabilization against agglomeration. The cumulative results have confirmed that MGF-[198]AuNPs are stable over extended periods of months. The inventors determined that the hydrodynamic size of gold nanoparticles depends on the amount of mangiferin encapsulated/coated around the gold nanoparticles. The higher the amount of mangiferin that encapsulates around nanoparticles, the higher the corona of mangiferin and the hydrodynamic size of MGF-AuNPs. Hydrodynamic sizes in the range~20-120 nm are readily achievable with the process described in the invention.

Synthesis.

An example experimental synthesis mixed 4.2 mg mangiferin (MGF) in 6 mL of doubly deionized (DI) water. The solution was stirred at 80° C. for 10 min to dissolve the MGF into water to get a yellow color clear solution. The gold salt (100 µl of 0.1 M) was added to the reaction mixture to produce the gold nanoparticles (AuNPs). The color was changed to ruby-red within a second, and developed the AuNPs. The AuNPs were centrifuged twice in 2 mL eppendorf tube at 12000 rpm at 12° C. for 15 min to remove the unreacted MGF and gold salt and was stored at 4° C. for further uses. The MGF-AuNPs were characterized by various instrumentation techniques like, UV-Vis spectrophotometry, Zetasizer Nano S90, TEM and AAS. The treatment concentrations were calculated based on the amount of MGF present in the MGF-AuNPs. The amount of MGF was calculated by atomic absorption spectrometry (AAS) technique. The MGF-AuNPs were tested in various experiments. Experiments have determined preferred ranges for synthesis methods consistent with the example in the previous paragraph. A preferred range of concentration of MGF is 1.6-3.3 mM.

A preferred range of the temperature for the reaction is a solution temperature of 80° C.-100° C., and more preferably 80° C.-90° C. A preferred range for the concentration of mangiferin in the reducing agent solution is in the range of 1.6-3.3 mM (millimoles). A preferred range for the concentration of gold salt is 1.7-4.3 mM (millimoles). A preferred range for stable storage of formed MGF-AuNP and MGF-[198]AuNP is 15-25° C. Experiments also showed that there is no need to remove the non-reactants, because reactants are fully consumed in these reactions. If needed, centrifuging the final product would suffice.

Details regarding the experiments and the materials will now be described.

Materials.

Mangiferin, Sodium tetrachloroaurate(III) dihydrate, MTT (3-(4,5-dimethyl thiazol-2-yl)-2,5-diphenyl tetrazolium), dynasore reagent and Chlorpromazine (CPZ) were obtained from Sigma (St. Louis, Mo., USA). RPMI (medium to culture live cancer cells), fetal calf serum and TryplE, Trypan blue, DAPI (4',6-diamidino-2-phenylindole), 2,7-dichlorofluorescin diacetate (DCFH-DA), mouse IgG isotype control, and laminin receptor antibody (MLuC5) were obtained from ThermoFisher Scientific, USA. FITC Annexin V Apoptosis Detection Kit I was obtained from BD Pharmingen, USA. X-22 anti-clathrin antibody (ab2731), anti-Caveolin-1 antibody (ab2910), anti-fibronectin antibody (ab18265), and in vitro angiogenesis assay kit (ab204726) were obtained from Abcam, USA. GFP-CERTIFIED® Apoptosis/Necrosis detection kit (ENZ-51002) was obtained from Enzo Life Sciences, Inc., USA. Phospho-NF-κB p65 (Ser536) (93H1) Rabbit mAb (Alexa Fluor®488 Conjugate) Kit was obtained from Cell Signaling Technology, USA. Double distilled water was used throughout the experiments described herein.

Cell Line.

The PC-3 (human prostate cancer cell line) was obtained from the American Type Culture Collection (ATCC; Manassas, Va.), and cultured by the University of Missouri Cell and Immunobiology Core facility using procedures recommended by ATCC.

Characterization of Nanoparticles.

Transmission electron microscope (TEM) images were obtained on a JEOL 1400 TEM (JEOL, LTE, Tokyo, Japan).

The absorption measurements were attained by UV-Vis spectrophotometer (Varian Cary 50 conc, USA). The hydrodynamic size and zeta potential were obtained by Zetasizer Nano S90 (Malvern Instruments Ltd. USA). The concentration of gold metal was calculated by atomic absorption spectrometry (AAS), Perkin Elmer, MA, USA.

Cell Viability Assay.

The effect of MGF-AuNPs and MGF on PC-3 cell viability was determined using MTT assay (Sigma). The intensity of developed color was measured by micro plate reader (Molecular device, USA) operating at 570 nm wavelength. Percent cell viability was calculated by using the formula: (T/C)×100, where C=Absorbance of control, T=Absorbance of treatment. The IC-50 values were calculated using the Origin software.

Apoptosis Assay.

PC-3 cells were incubated with different dilution of MGF and MGF-AuNPs for 24 h and the experiment was performed according to the manufacture's protocol (FITC Annexin V Apoptosis Detection Kit I). The samples were analyzed by FACScan flow cytometry (FACSort, Becton Dickinson, USA). For each sample, 30,000 ungated events were acquired.

Assessment of Apoptotic and Necrotic Cell Morphology.

PC-3 cells were incubated with different dilution of MGF and MGF-AuNPs for 24 h and the experiment was performed according to the manufacture's protocol (GFP-CERTIFIED® Apoptosis/Necrosis detection kit). The slides were prepared and visualized under fluorescence microscope with a dual filter set for Cyanine-3 (Ex/Em: 550/570 nm), 7-AAD (Ex/Em: 546/647) and GFP/FITC (Ex/Em: 488/514) (Olympus, USA).

In Vitro Anti-Angiogenesis Assay.

The in vitro anti-angiogenesis effect of MGF-AuNPs and MGF on PC-3 cell was determined using tube formation assay. The test was performed according the manufacture's protocol (In vitro angiogenesis assay kit). Briefly, matrigel was coated in 96 well plate and the plate was incubated for 30 min at 37° C. PC-3 cells and test samples were added into the same plate and incubated for 24 hr for tube formation analysis. The images were captured by fluorescence microscope, (Olympus, Center Valley, Pa., USA) at 4× after 24 hr.

Measurement of Reactive Oxygen Species (ROS).

The production of intracellular ROS was detected using 2,7-dichlorofluorescin diacetate (DCFH-DA). DCFH-DA passively enters the cell where it reacts with ROS to form highly fluorescent compound dichlorofluorescein (DCF). Briefly, PC-3 cells were incubated in 96-well plate for 24 hr and were exposed with 20 µM working solution of DCFH-DA for 30 min. After exposure to DCFH-DA, the cells were treated with test samples for 24 hr to measure the inhibition of ROS production. The plate was read by fluorescence plate reader at 485 nm excitation and 520 nm (Molecular device, USA).

NF-κB Measurement.

The Phospho-NF-κB p65 (Ser536) (93H1) Rabbit mAb (Alexa Fluor®488 Conjugate) Kit was used to study the effect MGF-AuNPs and free MGF on the expression of NF-κB. PC-3 cells were seeded into 6 well plate at a density of $8\times10^5$ cells/ml and were incubated for 24 h. The cells were treated with MGF-AuNPs (42 µM) and free MGF (42 µM) for 18 hr and post-treated with TNF-α (0.1 nM) for another 30 min at 37° C. The assay was performed as per kit instructions and the results were analyzed by FACScan flow cytometry (FACSort, Becton Dickinson, USA) with a minimum of 10 000 events being recorded.

Animal Studies.

All experiments of MGF-[198]AuNPs involving animals were approved by the Institutional Animal Care and Use Committees (IACUC) of the Harry S. Truman Memorial Veterans Hospital and the University of Missouri, and were performed according to the Guide for the Care and Use of Laboratory Animals. Imprinting control regions-severe combined immunodeficiency (ICR-SCID) female mice (from Taconic Farms, Hudson, N.Y.) were used for the therapeutic study. The mice used in our investigations weighed 24-27 g.

In Vivo Therapeutic Efficacy Study.

The severely compromised immunodeficiency (SCID) female mice were subcutaneously inoculated with $10\times10^6$ PC-3 cells (suspended in 0.1 mL of sterile DPBS and Matrigel® (2:1, v:v)) in the right hind flank under inhalation anesthesia (isoflurane/oxygen). After inoculation, tumors were allowed to grow for 3-4 weeks, at which time the tumors were measured by digital caliper measurements and calculated as length×width×height. The mice were randomly divided into three groups (n=7/group) with no significant difference in tumors volume, the day of randomization was considered day zero of therapy study. After two days of mice randomization, mice were treated as following: $1^{st}$ group of mice were directly injected into the prostate tumor with a single dose of MGF-[198]AuNPs (5.19 µg/30 µL), $2^{nd}$ group was injected with MGF (5.19 µg/30 µL) and control untreated group was injected with 30 µL of DPBS. The forth group (n=7) was kept as control group, without any treatment and tumor, and was served as a control for complete blood count (CBC) values and body weight measurements. Body weight and tumor volume measurements were observed twice per week for all groups, for approximately 3-4 weeks. Animals were sacrificed at the end of study or when tumors reached endpoint.

Statistical Analysis.

All experimental data were determined as mean±SEM. Statistical analysis was carried out using the one-way analysis of variances (ANOVA) using Graph Pad Prism software. $P<0.05$ was considered significant.

Results

Retention—Imaging showed efficient endocytosis of MGF-AuNPs within prostate cancer cells at sub nanomolar concentrations. Human and dog prostate tumors overexpress laminin receptors, as the laminin binding integrin α6β1 plays a major role in determining the aggressive phenotype of prostate tumor cells right from the initial stages of the disease all the way into its metastatic progression. Therefore, the propensity for endocytosis of MGF-AuNPs as observed in experiments provides compelling evidence of the laminin receptor specificity and selectivity of MGF-AuNPs. Laminin receptor specificity of MGF-AuNPs was confirmed by blocking laminin receptors using saturation assays through receptor blocking studies. These experimental findings, taken together, provide compelling evidence that the endocytosis of MGF-AuNPs is mediated through Lam 67R laminin binding integrin α6β1 receptors, which is shown by the images in FIGS. 4A-4D, as discussed further below.

Immunotherapeutic influence of MGF-AuNPs on NF-kB activity—A vexing medical problem in the care and treatment of prostate cancer patients is the intrinsic or acquired resistance to chemotherapeutic agents, including taxanes, anthracyclines and cisplatin drugs, which consequently trigger a cascade of therapeutic complications including intracellular drug inactivation, multi-drug resistance proteins, reduced cellular uptake of the drug, and enhanced tumor cancer cell DNA repair ultimately leading to evasion of apoptosis. Therefore, molecularly targeted therapies capable of inhibiting NF-κB signaling can re-sensitize cancer cells to apoptosis. This approach represents the next generation of precision medicine cancer therapeutics for treating prostate cancer. In experiments, we sought to determine whether the conjugation of mangiferin with gold nanoparticles would not only enhance tumor retention but also confer NF-κB targeting ability and ultimately reduce expression of MMP-9, thus stopping/decelerating prostate cancer invasiveness. We have measured transcription factor NF-kB after incubating MGF-AuNPs with PC-3 cells. The results from flow cytometry analysis indicated that MGF-AuNPs effectively blocked the TNF-α induced NF-kB activation significantly as compared to the untreated control and the free MGF treated groups. Fluorescence activity is an indicator of the effects of MGF-AuNps in suppressing NF-kB. The commercial fluorescence kits are designed in such a way that any decrease in fluorescence activity is indicative of the NF-kB suppression activity of MGF-AuNPs. These results are important because the efficient laminin receptor mediated endocytosis of MGF-AuNPs will provide clinically optimal therapeutic payloads of immunotherapeutic agent directly to primary prostate tumor cells to induce selective apoptosis. This effect is a direct consequence of MGF-AuNPs inhibition of NF-κB activation as well blockade of TNF-α induced p65 nuclear translocation.

Anti-Angiogenesis Properties of MGF-AuNPs—Immunotherapeutic effects of MGF-AuNPs in inhibiting NFkB has a direct effect in suppressing tumor growth through multiple mechanisms—direct suppression of tumor cell proliferation and the induction of tumor cell death coupled to the indirect effect of suppressing the tumor-induced angiogenesis. A tube/capillary formation assay was used to investigate the anti-angiogenesis effects of MGF-AuNPs. Images observed by phase contrast microscopy revealed that pre-incubation of HAECs with MGF-AuNPs inhibited the formation of capillaries at optimal 40 µM concentration doses, and experiments showed a preferred concentration range of 30-50 µM. In comparison, complete vasculature was observed in the control untreated cells as well as in cells treated with free MGF. The anti-angiogenesis effect of MGF-AuNPs was also pronounced as compared to the standard drug 'vinblastine'. These results taken together suggest that the anti-tumor action of MGF-AuNPs is driven through anti-angiogenesis mechanistic pathway suggesting multiplexed immune therapeutic actions of the preferred MGF-AuNPs nanotherapuetic agent.

Effect of MGF-AuNPs to initiate selective apoptosis of PC-3 cells—The cytotoxicity characteristics of MGF-AuNPs were tested with cell death by flow cytometry. MGF-AuNPs induced tumor cells into apoptotic programmed cell death, at a higher rate than free mangiferin. The findings corroborate the NF-κB mechanism of action. The studies also revealed that the anti-angiogenesis effect of MGF-AuNPs was pronounced as compared to the standard drug 'vinblastine'. These results suggest that the anti-tumor action of MGF-AuNPs is driven through the NF-κB pathway, and can provide a three-pathway effect of tumor apopstosis, anti-angiogenesis, and immunotherapeutic action.

MGF-AuNPs scavenge cellular reactive oxygen species (ROS) and catalyze apoptosis—The role of ROS in apoptosis induced by physiological stimuli such as death receptor activation continues to be controversial. Several studies have suggested enhancement of apoptosis as a direct consequence of depletion of ROS in cells lacking mitochondrial DNA, which are deficient in respiration and mitochondrial oxidative phosphorylation, the source of ROS during apoptosis. It is also interesting to note that ROS formation has been linked with the progression of, pro-apoptotic factors, Fas-induced apoptosis due to the protective effect of extracellular thiols such as reduced glutathione (GSH) and N-acetyl-1-cysteine (NAC). The efficient and selective endocytosis ability of MGF-AuNPs within PC-3 cells, resulting in excellent apoptotic cell death, prompted us to investigate their role in modulating ROS in cancer cells. We measured ROS by initiating oxidation of DCFDA into DCF in the mitochondria by various peroxide and nitric oxide derived reactive intermediates in PC-3 cells. The levels of ROS in PC-3 cells after treatment with MGF-AuNPs showed a marked decrease thus suggesting that MGF-AuNPs indeed inhibit the production of ROS. Although the results obtained from our studies suggested that both the MGF-AuNPs and free MGF are effective in inhibiting ROS production, the enhanced bioavailability of MGF, when it is conjugated to gold nanoparticles, and the synergistic role of gold nanoparticles as a ROS scavenger provide profound enhanced benefits in achieving efficient mitochondrial dysfunction and thus triggering mitochondria-mediated apoptosis in cancer therapeutics.

In vivo therapeutic efficacy studies of directly injected MGF-$^{198}$AuNPs—To validate NF-κB suppression and the associated M2-TAM targeting abilities of MGF-$^{198}$AuNPs, we performed in vivo therapeutic efficacy studies of MGF-$^{198}$AuNPs in SCID mice implanted with prostate tumor (PC-3) xenografts. The therapeutic efficacy data of MGF-$^{198}$AuNPs corroborate its ability to induce apoptosis because tumors harvested from the treatment group consisted largely of apoptotic cells, indicating extensive programmed tumor cell death. The tolerability of the MGF-$^{198}$AuNPs in vivo has been established by monitoring the body weight and blood parameters in the SCID mice study in both treated and control groups of animals. The treatment group showed only transient weight loss with recovery to normal weight without any early terminations. White and red blood cell, platelet, and lymphocyte levels within the treatment group resembled those of the control mice without tumors. The overall health status and blood measures of the MGF-$^{198}$AuNPs-treated animals indicated that this new therapeutic modality was not only effective, but also well tolerated. These findings support the effectiveness of intralesional therapy of prostate cancer using MGF-$^{198}$AuNPs in managing the primary tumor location, a critical step in converting active disease to static disease. The compelling immune modulated therapeutic efficacy data in mice provide compelling evidence for use in treating human patients with prostate and various other tumors.

MGF-AuNPs increase IL-12 to IL-10 ratios by targeting macrophage—Imaging revealed conclusive evidence showing polarization of RAW 264.7 macrophages to M1 phenotype after treatment with MGF-AuNPs. We observed that RAW 264.7 macrophages treated with MGF-AuNPs strongly polarized macrophages to M1 phenotype. As a control, when starch conjugated gold nanoparticles were used in these experiments, we saw no polarization of macrophages to M1 phenotype thus corroborating with our hypothesis on the important role of MGF-AuNPs to polarize to M1 antitumor phenotype and that the polarization effects on macrophages are sustained under in vivo profiles too offering anti-tumor effects.

Observation 9: MGF-AuNPs treated RAW 264.7 macrophages inhibit the proliferation of canine prostate tumor cells—We also observed that macrophages treated with MGF-AuNPs inhibited the proliferation of canine ACE-1 prostate tumor cells, which further corroborated the hypothesis that MGF-AuNPs can be used to target macrophages to inhibit tumor growth and development. Based on these conclusive experimental data, we infer that the mechanism of anti-tumor effects of MGF-AuNPs are based on its immunomodulatory efficacy of targeting macrophages of prostate tumor cells and thus serves as a new immunotherapeutic agent for treating human prostate and various tumors.

In Vivo Therapeutic Efficacy Studies of Directly Injected MGF-$^{198}$AuNPs

MGF-$^{198}$AuNPs provide the best opportunity for therapeutic effect, and have been demonstrated as having the excellent retention of the MGF-AuNPs in the experiments above. The MGF-$^{198}$AuNP experiments will now be discussed along with additional data concerning MFG-AuNP cell intake and retention.

Synthesis and Characterization of Radioactive MGF-$^{198}$AuNPs.

MGF-$^{198}$AuNPs was produced by direct irradiation of natural gold foil. Gold foil was irradiated at a neutron flux of 8×10$^{13}$ n/cm$^2$/s. Irradiation times varied from 6 to 40 h. After irradiation, the radioactive foil was dissolved in 400 μL of aqua regia and heated to bring it to near dryness. Then, 400 μL of 0.05 M HCl was added three times and heated to azeotrope off the nitric acid. Next, the product was dissolved in a desired volume of water to make the final solution of $^{198}$Au, which was used for the production of MGF-$^{198}$AuNPs. The radioactive gold salt solution ($^{198}$Au) as prepared above was mixed with NaAuCl$_4$ to form radioactive gold precursor. A radioactive gold precursor is prepared by mixing specific mass of $^{198}$Au with specific mass of gold salt results in a radioactive gold precursor that has total mass of radioactive$^{198}$Au and non-radioactive Au of 0.66 mg and a particular activity. The mass of $^{198}$Au that is mixed with NaAuCl$_4$ is determined according to the required activity of final solution of nanoparticles. For therapeutic study, the mass of $^{198}$Au was 0.082 mg (this mass was chosen because it has the required activity which is 13 mCi). Then 0.082 mg of $^{198}$Au was mixed with gold salt that has mass of gold equal to 0.578 mg in order to make the total mass of gold in the solution equal to 0.66 mg for 2 mL gold nanoparticles preparation. If less activity is needed, then the mass of $^{198}$Au would be decreased and mass of gold within gold salt would be increased, so that the total mass of gold would be 0.66 mg.

Reaction kinetics at the macroscopic levels is different as compared to reactions when the reactants are present in tracer level concentrations. Therefore, a slightly modified approach, as compared to the synthetic protocol used for the synthesis of non-radioactive MGF-AuNPs as described above, has been developed for the synthesis of the corresponding radioactive MGF-$^{198}$AuNPs. Specifically, the solution temperature range, concentration of gold salts, concentration of mangiferin, etc. can be the same. A preferred protocol for the production of radioactive MGF-$^{198}$AuNPs consisted of dissolving 1.6 mg of MGF in 2 mL of milli-Q water at room temperature for 10 minutes, stirred and heated at 99° C. At this temperature, radioactive gold precursor solution ($^{198}$Au+NaAuCl$_4$) that has desired activity (390 μCi-13mCi) was added to the MGF solution resulting in immediate color change from pale yellow to red purple color. After that, the solution was stirred for an additional hour at room temperature.

The formation of radioactive gold nanoparticles was characterized by measuring the surface plasmon resonance wavelength ($\lambda_{max}$) using UV-Vis spectroscopy. Radio-TLC was performed to estimate the yield of radioactive gold nanoparticles. The procedure was performed by adding 1 μL of nanoparticles solution to the origin of cellulose TLC plate. After 5 min, TLC plate was developed in 4 mL of methanol containing two drops of concentrated HCl. Then the yield of radioactive gold nanoparticles was measured using a Bio-scan, free $^{198}$Au precursor moves to the solvent front ($R_f=1$) whereas $^{198}$Au-nanoparticles remain at the origin ($R_f=0$). The UV-vis spectroscopy measurements showed that $\lambda_{max}$ was in the range of 530-535 nm and Radio-TLC confirmed that over 97% of $^{198}$Au was present in the nanoparticulate form. Stability study results showed that MGF-$^{198}$AuNPs remained stable out to 7 days.

TABLE 1

Physiochemical data parameters of mangiferin conjugated gold nanoparticles (MGF-AuNPs).

| UV visible spectrophotometry | Zeta size | Zeta potential | TEM | AAS Au and MGF conc/mg of MGF-AuNPs | |
|---|---|---|---|---|---|
| 530 nm | 60 ± 3 nm | −50.5 ± 2 mV | 35 ± 2 nm | 0.320 mg of Au | 0.173 mg of MGF |

Tumor Retention and Therapeutic Efficacy Studies MGF-AuNPs

Because of radioactivity, UV-visible spectrophotometry measurement of the Physiochemical data for the radioactive gold nanoparticles is difficult to impossible. For this reason, spectrophotometry data measured for the non-radioactive gold nanoparticles (MGF-AuNPs), shown in Table 1, is used and serves as an excellent model for the size, zeta potential and concentration of radioactive gold nanoparticles. The tumor uptake and retention study also included intratumoral injection of radioactive MGF-$^{198}$AuNPs in PC-3 tumor bearing SCID mice (4 μCi/30 μL for each tumor) and analysis of radioactivity in tumor as well as various organs post euthanasia of animals at 30 min, 1, 2, 4, and 24 h. Intratumoral administration MGF-$^{198}$AuNPs in prostate tumor bearing mice showed that nearly 80% of the injected dose (ID) of MGF-$^{198}$AuNPs was retained in prostate tumors up to 24 h, and it was nearly constant from 30 min to 24 h. (% ID) was 80.98±13.39% at 30 min decreasing to 79.82±10.55% at 24 h. There was low leakage and subsequent uptake of MGF-$^{198}$AuNPs in the liver, the (% ID) in liver was 4.05±5.27% at 30 min increasing to 10.65±8.31% at 24 h.

The therapeutic efficacy of MGF-$^{198}$AuNPs was evaluated using human prostate tumor-bearing SCID mice. There were two groups of mice bearing prostate tumors with comparable size. A third group was evaluated also prostate tumor bearing but with larger volumes. The first and third groups were injected intratumorally with a single dose of MGF-$^{198}$AuNP (160 μCi/30 uL per tumor) whereas the second group was injected intratumorally with 30 uL of saline and served as control group.

Figure 2:
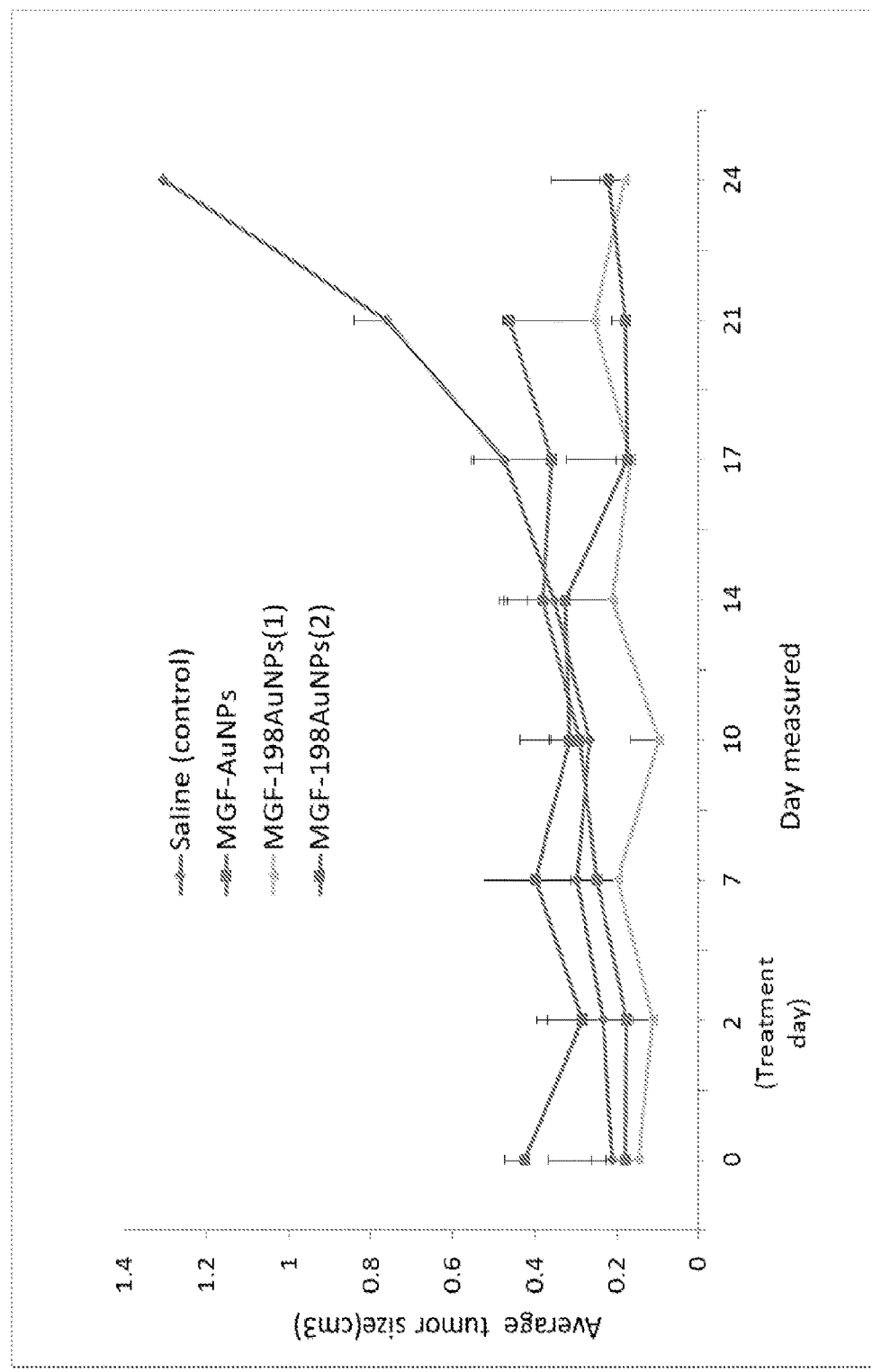
FIG. 2 includes the therapeutic efficiency data in controlling tumor size of preferred MGF-$^{198}$AuNPs and MGF-AuNP compared to a control group.

Results of the therapy study indicated radioactive MGF-$^{198}$AuNPs have the ability to reduce tumor volume in comparison to saline control group. By three weeks post treatment, tumor volume of control group (saline) was much larger than the tumor volume of the groups injected with radioactive nanoparticles (1.31±0.00 cm$^3$ for control versus 0.18±0.17 cm$^3$ for MGF-$^{198}$AuNPs 1, and 0.22±0.02 cm$^3$ for MGF-$^{198}$AuNPs2). FIG. 2 shows that the tumor size for the control group increases greatly after 17 days and continues to grow at 24 days. The non-radioactive MGF-AuNPs provide some control of growth, showing an average size of 0.4 cm$^3$ at 21 days, which is half the average size (0.8 cm$^3$) of the control group at 21 days. Therapeutic efficacy study of MGF-$^{198}$AuNPs. Both sets of $^{198}$AuNPs (1) and $^{198}$AuNPs (2) provide the best suppression of tumor growth, with the average tumor size remaining slight above or below the original tumor size at zero days through 24 days.

The right hind flank of severe combined immunodeficiency (SCID) female mice were subcutaneously inoculated with 10×10$^6$ PC-3 cells suspended in 0.1 mL of sterile DPBS and Matrigel® (2:1, v:v) under inhalation anesthesia (isoflurane/oxygen). After inoculation, tumors were allowed to grow for 4 weeks. The tumor volumes were measured by digital caliper measurements and was calculated as length× width×height. Then, the mice were randomly divided into two groups with no significant difference in tumors volume; the additional third group (for therapy) was added in which the tumor volume was larger than the other groups. The day of randomization was considered day 0 for the therapy study. At day two, mice were treated as following, second group (n=6) and third group (n=3) of mice were directly injected into the prostate tumor with a single dose of MGF-$^{198}$AuNPs (160 μCi/30 μL per tumor), whereas 30 μL of DPBS was directly injected into the prostate tumor of the first group (n=6) of mice. The first group was considered as untreated control group. The fourth group (n=7), which is normal and did not bear any tumor, received no treatment and served as the control for complete blood count (CBC) analysis. Post injection, body weight and tumor volume measurements were taken twice a week for all groups, for approximately 5 weeks. Animals were sacrificed at the end of study period or when tumors reached endpoint or based on their body weight loss. At the time of sacrifice, blood samples were collected from each animal and transported to IDEXX analyzer for CBC analysis and organs of interest of the 2$^{nd}$ and 3$^{rd}$ groups were harvested to measure the radioactivity levels using NaI well counter. FIG. 2 shows the therapeutic efficiency data of MGF-$^{198}$AuNPs.

In-Vitro Stability and Dilution Study of MGF-AuNPs.

Figure 3:
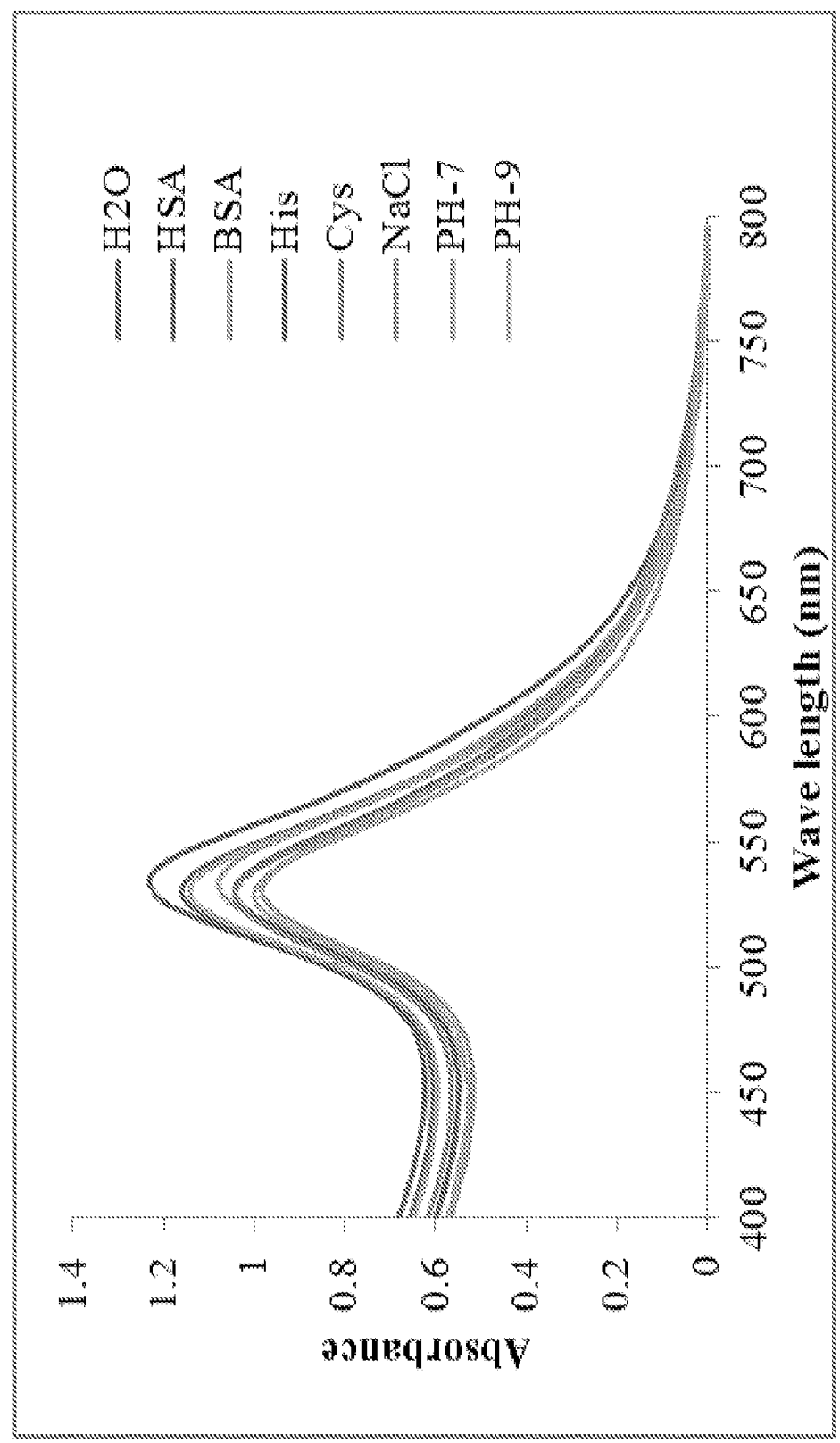
FIG. 3 includes UV-Vis spectra data showing the in vitro stability of MGF-AuNPs in different media, and the data serves as a model for in vitro stability of MGF-$^{198}$AuNPs.

As noted above, MGF-AuNPs were used as a model for MGF-$^{198}$AuNPs to obtain certain spectra. The stability of MGF-AuNPs were confirmed by mixing gold nanoparticles to aqueous solutions of 1% NaCl, 0.5% cysteine, 0.2 M histidine, 0.5% human serum albumin (HSA), 0.5% bovine serum albumin (BSA), pH7, and pH9. FIG. 3 shows the UV-Vis spectra showing the in vitro stability of MGF-AuNPs in the various media. The stability of the conjugates was measured by monitoring the UV absorbance over a period of 1 h, 4 h, 24 h, 48 h and 1 week. A negligible change in UV-vis plasmon band confirmed the retention of nanoparticulate composition in all mixtures (FIG. 3). We also confirmed the stability of MGF-AuNPs at different dilutions by UV-visible spectrophotometry, which is very important for biomedical application.

Cell Internalization Studies

To investigate the mode of action of MGF-AuNPs in to the PC-3 cells, cells was treated with various inhibitors to confirm the clathrin mediated endocytosis pathway. The following two techniques were used to measure the cellular internalization.

Figure 4B:
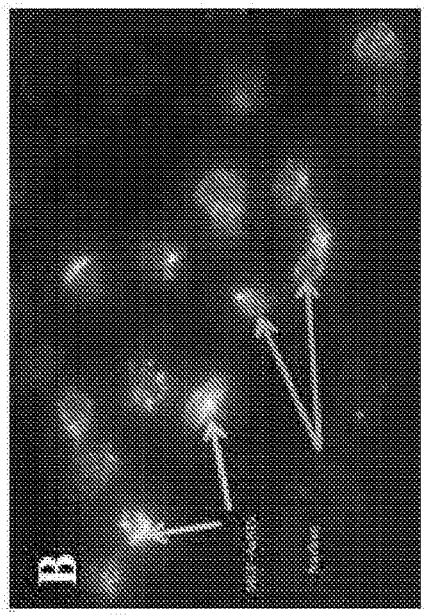
FIGS. 4A-4D are dark field images showing intake of MGF-AuNP into prostate cancer PC-3 cells two hours after treatment, which images also serve as model for intake and retention of MGF-$^{198}$AuNPs.
Figure 4D:
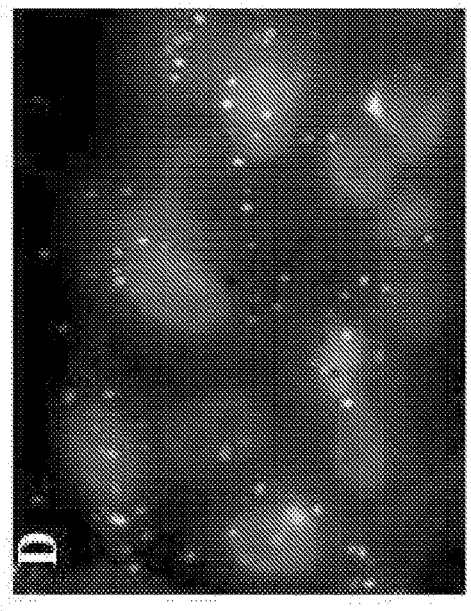
Figure 4A:
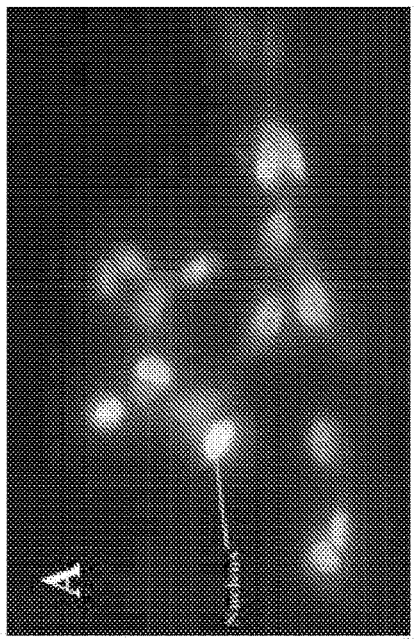
Figure 4C:
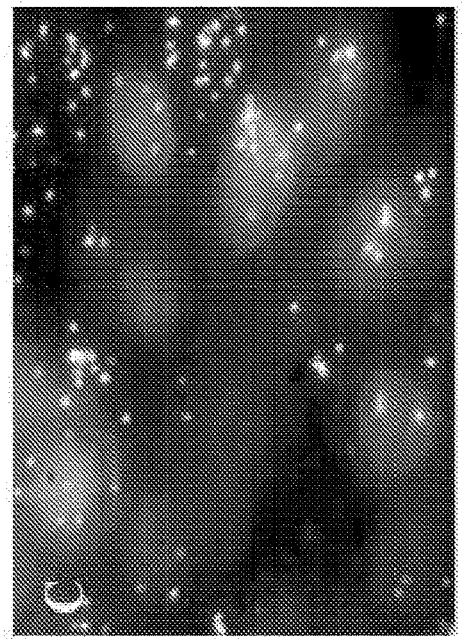

Dark Field Microscopy—to understand cellular trafficking pathway into the PC-3 cells, we used various inhibitors to confirm the clathrin-mediated endocytosis. Ultra clean and sterile cover slips were kept in 6 well plates. The PC-3 (8×10$^5$ cells) were seeded into 6 well plates in RPMI medium and incubated for 24 h in CO$_2$ incubator at 37° C. The cells were treated with the inhibitors respectively: PBS (control), clathrin pathway using 28 μM chlorpromazine, laminin receptor pathway by blocking laminin receptor onto PC-3 using antibody LR. The cells were treated with chlorpromazine for 30 min and were incubated in CO$_2$ incubator at 37° C. Cells were treated with ABLR for 1 hr and kept in CO$_2$ incubator at 37° C. After the incubation time cells were washed with PBS followed by the incubation with MGF-AuNPs (12.5 μg/ml) for 2 hr in CO$_2$ incubator at 37° C. After incubation, cells were washed 10-12 times with 1×PBS, and fixed with 4% para-formaldehyde (PFA). Cells were further washed 2-3 times with 1×PBS. Slides were prepared by using DAPI nuclear dye and observed with CytoViva dark field microscope coupled with dual mode fluorescence. Cell morphology was initially observed, followed by uptake of nanoparticles. Images were captured via Dage Imaging Software. FIGS. 4A-4D shows the dark field imaging results for intake into prostate cancer PC-3 cells two hours after treatment. FIG. 4A shows untreated cells. FIG. 4B shows cells treated with 25 μg/ml MGF-AuNPs. FIG. 4C shows the effect of AuNPs after blocking the CME pathway by Chlorpromazine hydrochloride. FIG. 4D shows the effect of AuNPs internalization after blocking the laminin receptor antibody.

Figure 5A:
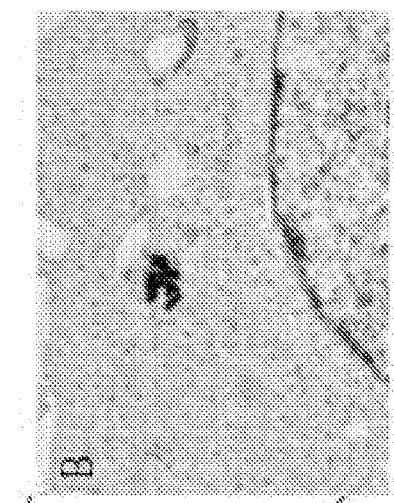
FIGS. 5A-5D are TEM microscope images of MGF-AuNP with PC-3 cells, which images also serve as a model for intake and retention of MGF-$^{198}$AuNPs.
Figure 5B:
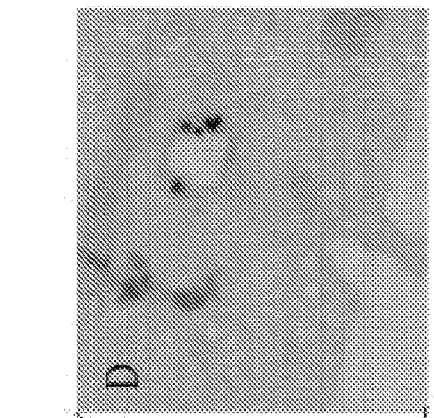
Figure 5C:
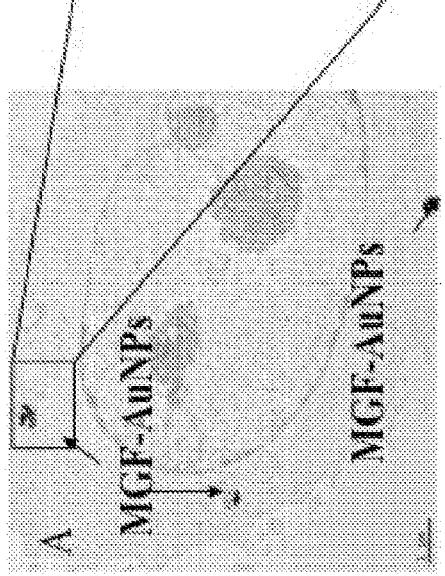
Figure 5D:
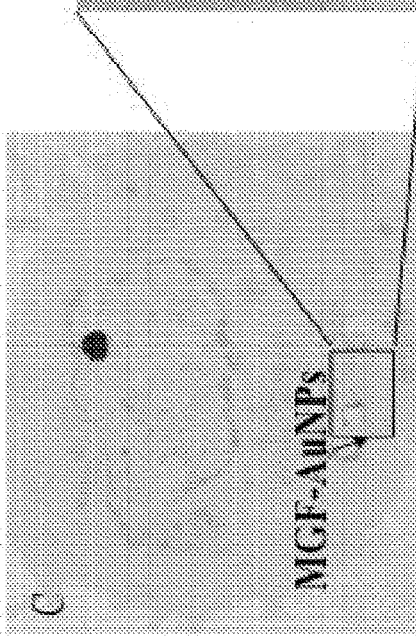

TEM study. This technique was used to confirm the detail internalization of AuNPs inside the cells to confirm that if it is inside the cytoplasm or in the nucleus. The PC-3 cells (8×10$^5$ cells) were seeded into 6 well plates in RPMI medium separately and allowed to adhere for 24 h in CO$_2$ incubator at 37° C. To confirm the laminin receptor affinity of MGF-AuNPs, we blocked the laminin receptor onto the PC-3 cells by using the ABLR. The cells was treated with control PBS and ABLR (10 μg/ml) for 1 hr and incubated in CO$_2$ incubator at 37° C. The cells was washed with PBS and treated with MGF-AuNPs with the concentration 25 μg/ml followed by 2 hr of incubation. The cells were washed 10 times with PBS, centrifuged into small pellets, and fixed with 2% glutaraldehyde 2% paraformaldehyde in sodium cacodylate buffer (0.1 M). The cells were further fixed with 1% buffered osmium tetraoxide in 2-Mercaptoethanol buffer and dehydrated in graded acetone series and embed in Epon-Spurr epoxy resin. Sections were cut at 85 nm using a diamond knife (Diatome, Hatfield Pa.). The sections were stained with Sato's triple lead stain and 5% aqueous uranyl acetate for organelle visualization. The prepared samples were examined on JEOL 1400 TEM microscope (JEOL, Peabody, Mass.) operated at 80 kV at the University of Missouri's Electron Microscopy Core Facility. FIGS. 5A-5D show the TEM results. FIG. 5A shows cells treated (2 hours post-treatment) with 25 μg/ml MGF-AuNPs. FIG. 5B shows a magnified view of FIG. 5A. FIG. 5C shows the effect of AuNPs after blocking after blocking the laminin receptor antibody. FIG. 5D is a magnified view of FIG. 5C.

$^{198}$Au provides a desirable beta energy emission and half-life that destroys tumor cells/tumor tissue ($\beta_{max}$=0.96 MeV; half-life of 2.7 days). Its penetration range (up to 11 mm in tissue or up to 1100 cell diameters) is sufficiently long to provide cross-fire effects to destroy tumor cells, but short enough to minimize radiation exposure to tissues near the capsule periphery. The present MGF-$^{198}$AuNP have been demonstrated via the experiments to form effective tumor-specific radioactive gold nanoparticles. The present solutions of MGF-$^{198}$AuNP, especially when directly injected, are tailor-made for Auger, Coster-Kronig, transitions with subcellular ranges (nanometers) as Au-$^{198}$ decays by electron capture and/or internal conversion to extremely low-energy electrons through Auger effects—all within the tumor capsule giving potent therapeutic doses. The ejection of electrons leaves the decaying atoms transiently in a state of high positive charge as the burst of low-energy electrons results in highly localized energy deposition (106-109 cGy). The efficacy of the present invention has been demonstrated from the treatment of prostate tumors in mice through intratumoral delivery of MGF-$^{198}$AuNP. The MGF-$^{198}$AuNP provide compelling evidence of a new generation of cancer therapy agents that are capable of producing strong tumor specific and tumor selective therapeutic effects through Auger electron-emitting effects of MGF-$^{198}$AuNP radionuclide in treating various forms of human cancers including prostate, breast, pancreatic, liver etc. Preferred methods of the invention include direct injection into solid tumors, however, the MGF-$^{198}$AuNP have therapeutic efficacy for treating various solid, liquid, localized and metastatic tumors comprising of breast, cervical, glioblastomas, liver, melanoma, osteosarcomas, pancreatic, prostate and all related tumors and neoplastic diseases in humans and animals. For treatment of solid, liquid, localized and metastatic tumors, the MGF-$^{198}$AuNP can be ingested, and can be functionalized for affinity to cancer cells as are previously mentioned GA-$^{198}$AuNPs and other AuNPs have been functionalized for affinity.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. A method for forming encapsulated gold nanoparticles, the method comprising:
    mixing mangiferin (1,3,6,7-tetrahydroxyxanthone-C2-D glucoside) into one of distilled and/or de-ionized water and a mixture of water and alcohol to form a reducing agent solution having synergistic xanthanoid and glucose units from the mangiferin as active reducing agents;
    mixing gold salts into the reducing agent solution, wherein the reducing agent solution consists of the mangiferin, the water or mixture and the gold salts;
    permitting reaction of the gold salts with the reducing agents, in the absence of any other reducing agent, to form a nanoparticle solution of stabilized, biocompatible gold nanoparticles coated with mangiferin.

2. The method of claim 1, wherein the liquid medium consists of distilled and/or de-ionized water.

3. The method of claim 1, wherein the liquid medium consists of an alcoholic medium or a mixture of water and alcohol.

4. The method of claim 1, wherein the gold salts consist of AuCl$_4$.

5. The method of claim 1, wherein the concentration of mangiferin in the reducing agent solution is in the range of 1.6-3.3 mM.

6. The method of claim 5, wherein the concentration of gold salt is 1.7-3.4 mM.

7. The method of claim 6, wherein said permitting reaction is conducted at an agent solution temperature of 80° C.-100° C.

8. The method of claim 1, wherein the gold salts comprise radioactive gold salts.

9. The method of claim 8, further comprising preliminary steps of preparing radioactive gold foil and dissolving the radioactive gold foil intoaqua regia and drying the liquid to produce radioactive gold istope in powdered form (Au-198), drying the $^{198}$Au powder, and dissolving the dried $^{198}$Au powder into the liquid medium, and mixing in NaAuCl$_4$ to form the radioactive gold salts in the liquid medium.

10. The method of claim 9, wherein preparing the radioactive gold foil comprises irradiating natural gold foil with a neutron flux.

11. The method of claim 9, wherein the mass ratio of $^{198}$Au to NaAuCl$_4$ is selected to set an activity level.

12. A method of therapy, comprising intratumorally directly injecting the nanoparticle solution formed according to claim 9 into a solid tumor.

13. A method of therapy, comprising intratumorally directly injecting the nanoparticle solution formed according to claim 1 into a solid tumor.

14. The cancer therapy method of claim 13, wherein the tumor comprises a human prostate cancer tumor.

15. The cancer therapy method of claim 9, wherein the mangiferin encapsulated gold nanoparticles comprise $^{198}$Au nanoparticles having core sizes of ~5-50 nm.

16. The cancer therapy method of claim 15, wherein a mass of $^{198}$Au is selected to set an activity level.

* * * * *